(12) United States Patent
Kendrick

(10) Patent No.: US 11,172,952 B2
(45) Date of Patent: Nov. 16, 2021

(54) SURGICAL APPARATUS

(71) Applicant: COVIDIEN LP, Mansfield, MA (US)

(72) Inventor: Stephen M. Kendrick, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 583 days.

(21) Appl. No.: 15/350,237

(22) Filed: Nov. 14, 2016

(65) Prior Publication Data

US 2017/0056037 A1    Mar. 2, 2017

Related U.S. Application Data

(62) Division of application No. 14/041,995, filed on Sep. 30, 2013, now Pat. No. 9,498,281.

(Continued)

(51) Int. Cl.
*A61B 17/29* (2006.01)
*A61B 18/14* (2006.01)
*A61B 17/295* (2006.01)

(52) U.S. Cl.
CPC ............ *A61B 17/29* (2013.01); *A61B 17/295* (2013.01); *A61B 18/1445* (2013.01);
(Continued)

(58) Field of Classification Search
CPC .... A61B 2017/2932; A61B 2017/2933; A61B 2017/2934; A61B 17/29;
(Continued)

(56) References Cited

U.S. PATENT DOCUMENTS

D249,549 S    9/1978  Pike
D263,020 S    2/1982  Rau, III
(Continued)

FOREIGN PATENT DOCUMENTS

CN    201299462 Y    9/2009
DE      2415263 A1   10/1975
(Continued)

OTHER PUBLICATIONS

Extended European Search Report dated Mar. 17, 2014 for EP 13 19 3635.
(Continued)

*Primary Examiner* — Ronald Hupczey, Jr.
*Assistant Examiner* — Bradford C. Blaise
(74) *Attorney, Agent, or Firm* — Carter, DeLuca & Farrell LLP

(57) ABSTRACT

A surgical apparatus includes a housing that supports a shaft assembly. The shaft assembly defines a longitudinal axis therethrough and includes coaxially aligned outer and inner shaft members. The inner shaft member is movable within the outer shaft member. An end effector includes a pair of jaw members disposed at a distal end of the outer shaft. At least one of the jaw members is pivotably coupled to the outer shaft and is movable between open and clamping configurations for grasping tissue. The inner shaft contacts a proximal end of the moveable jaw member to maintain the movable jaw member in the open configuration and is slidable against the movable jaw member to move the moveable jaw member between the open configuration and clamping configuration.

17 Claims, 12 Drawing Sheets

Related U.S. Application Data

(60) Provisional application No. 61/730,399, filed on Nov. 27, 2012.

(52) U.S. Cl.
CPC .. *A61B 18/1447* (2013.01); *A61B 2017/2901* (2013.01); *A61B 2017/2932* (2013.01); *A61B 2017/2933* (2013.01); *A61B 2017/2934* (2013.01); *A61B 2018/1455* (2013.01); *F04C 2270/0421* (2013.01)

(58) Field of Classification Search
CPC .... A61B 2017/2901; A61B 2017/2936; A61B 2017/2938; A61B 17/295; A61B 18/1445; A61B 18/1447; A61B 18/1455
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,263,967 A * | 11/1993 | Lyons, III .............. A61B 17/29 294/115 |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,496,317 A * | 3/1996 | Goble .................. A61B 17/29 600/564 |
| D384,413 S | 9/1997 | Zlock et al. |
| 5,700,275 A * | 12/1997 | Bell .................. A61B 17/2909 606/208 |
| H1745 H | 4/1998 | Paraschac |
| D402,028 S | 12/1998 | Grimm et al. |
| D408,018 S | 4/1999 | McNaughton |
| D416,089 S | 11/1999 | Barton et al. |
| 6,019,780 A * | 2/2000 | Lombardo ......... A61B 17/1608 600/564 |
| 6,053,933 A * | 4/2000 | Balazs .................. A61B 17/29 606/205 |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,464,702 B2 | 10/2002 | Schulze et al. |
| D465,281 S | 11/2002 | Lang |
| D466,209 S | 11/2002 | Bon |
| 6,500,176 B1 | 12/2002 | Truckai et al. |
| 6,585,735 B1 | 7/2003 | Frazier et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| 7,189,233 B2 | 3/2007 | Truckai et al. |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,955,332 B2 * | 6/2011 | Arts ................... A61B 17/2812 606/174 |
| D649,249 S | 11/2011 | Guerra |
| D649,643 S | 11/2011 | Allen, IV et al. |
| D661,394 S | 6/2012 | Romero et al. |
| 9,005,200 B2 | 4/2015 | Roy et al. |
| 9,017,372 B2 | 4/2015 | Artale et al. |
| 9,498,281 B2 | 11/2016 | Kendrick |
| 2007/0173814 A1 | 7/2007 | Hixson et al. |
| 2009/0076506 A1 | 3/2009 | Baker |
| 2009/0259248 A1 * | 10/2009 | Ganter ................... A61B 17/29 606/205 |
| 2011/0009864 A1 * | 1/2011 | Bucciaglia ......... A61B 17/2909 606/52 |
| 2011/0034918 A1 * | 2/2011 | Reschke ............ A61B 17/2812 606/41 |
| 2011/0060333 A1 * | 3/2011 | Mueller ............... A61B 17/295 606/46 |
| 2011/0184405 A1 * | 7/2011 | Mueller .............. A61B 18/1445 606/41 |
| 2011/0251612 A1 | 10/2011 | Faller et al. |
| 2013/0079762 A1 | 3/2013 | Twomey et al. |
| 2013/0267950 A1 | 10/2013 | Rosa et al. |

FOREIGN PATENT DOCUMENTS

| | | |
|---|---|---|
| DE | 2514501 A1 | 10/1976 |
| DE | 2627679 A1 | 1/1977 |
| DE | 3423356 A1 | 1/1986 |
| DE | 3612646 A1 | 4/1987 |
| DE | 3627221 A1 | 2/1988 |
| DE | 8712328 U1 | 2/1988 |
| DE | 4303882 A1 | 8/1994 |
| DE | 4403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 102004026179 A1 | 12/2005 |
| DE | 202007009165 U1 | 8/2007 |
| DE | 202007009317 U1 | 8/2007 |
| DE | 202007009318 U1 | 8/2007 |
| DE | 102006028001 A1 | 12/2007 |
| DE | 202007016233 U1 | 1/2008 |
| DE | 102008018406 B3 | 7/2009 |
| EP | 1159926 A2 | 12/2001 |
| EP | 1281878 A1 | 2/2003 |
| EP | 1810625 A1 | 7/2007 |
| JP | 61501068 | 9/1984 |
| JP | 6502328 | 3/1992 |
| JP | 55106 | 1/1993 |
| JP | 540112 | 2/1993 |
| JP | 6030945 B2 | 2/1994 |
| JP | 6121797 | 5/1994 |
| JP | 6285078 | 10/1994 |

(56) References Cited

FOREIGN PATENT DOCUMENTS

| JP | 6343644 | 12/1994 |
|---|---|---|
| JP | 6511401 | 12/1994 |
| JP | 7265328 | 10/1995 |
| JP | 856955 | 3/1996 |
| JP | 8317936 | 3/1996 |
| JP | 8289895 | 5/1996 |
| JP | 8252263 | 10/1996 |
| JP | 8317934 | 12/1996 |
| JP | 910223 | 1/1997 |
| JP | 9000538 | 1/1997 |
| JP | 9122138 | 5/1997 |
| JP | 1024051 | 1/1998 |
| JP | 10000195 | 1/1998 |
| JP | 10155798 | 6/1998 |
| JP | 1147149 | 2/1999 |
| JP | 1147150 | 2/1999 |
| JP | 11070124 | 3/1999 |
| JP | 11169381 | 6/1999 |
| JP | 11192238 | 7/1999 |
| JP | 11244298 | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 20018944 | 1/2001 |
| JP | 200129355 | 2/2001 |
| JP | 200129356 | 2/2001 |
| JP | 2001128990 A | 5/2001 |
| JP | 2001190564 A | 7/2001 |
| JP | 20013400 | 11/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 05110264 A3 | 4/2006 |
| WO | 2008040483 A1 | 4/2008 |
| WO | 2011018154 A1 | 2/2011 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 39, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. Jul. 1, 2001 pp. 21-24.
Levy et al., "Update on Hysterectomy—New Technologies and Techniques" OBG Management, Feb. 2003.

(56) References Cited

OTHER PUBLICATIONS

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

\* cited by examiner

SURGICAL APPARATUS

CROSS REFERENCE TO RELATED APPLICATIONS

The present application is a divisional of U.S. patent application Ser. No. 14/041,995, filed Sep. 30, 2013, and which issued as U.S. Pat. No. 9,498,281 on Nov. 22, 2016, which claims the benefit of and priority to U.S. Provisional Application Ser. No. 61/730,399, filed Nov. 27, 2012. The entire contents of each of these applications are incorporated herein by reference.

BACKGROUND

Technical Field

The present disclosure relates to surgical apparatuses. More particularly, the present disclosure relates to surgical apparatuses including jaw members configured to grasp, manipulate and/or treat tissue.

Description of Related Art

Surgical apparatuses utilized to grasp, manipulate and/or treat tissue are known in the medical art. For example, endoscopic electrosurgical forceps utilize an end effector having one or more moveable jaw members that are configured to grasp tissue and, subsequently, treat the tissue via one or more suitable types of energy, e.g., radio frequency (RF). In certain instances, the movable jaw member(s) is/are actuated to move from an open configuration for positioning tissue between the jaw members to a closed configuration for grasping tissue for subsequent treatment thereof. In certain instances, the treated tissue may be severed.

A drive member, typically, couples to the moveable jaw member(s) via one or more cam pins operably coupled to corresponding cam slots disposed on the moveable jaw member(s). As is conventional in the art, the cam slot(s) is/are provided at a proximal end of the moveable jaw member(s) via one or more suitable methods. For example, and in one particular instance, the cam slot(s) may be machined out of the movable jaw member(s).

As can be appreciated, the machining process may add to the overall manufacturing costs of the forceps. Moreover, and in the instance where the forceps is configured to sever tissue, a knife blade is typically provided with "webbing" that allows the knife blade to pass around (or over) the cam pin(s) on the moveable jaw member(s). As can be appreciated, providing a knife blade that includes webbing may also add to the overall manufacturing costs of the forceps.

SUMMARY

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

As defined herein, a surgical apparatus includes without limitation graspers, forceps of any type, probes and the like.

An aspect of the present disclosure provides a surgical apparatus, e.g., an endoscopic electrosurgical forceps. The surgical apparatus includes a housing that supports a shaft assembly. The shaft assembly defines a longitudinal axis therethrough and includes coaxially aligned outer and inner shaft members. The inner shaft member is movable within the outer shaft member. An end effector includes a pair of jaw members disposed at a distal end of the outer shaft member and pivotably coupled to one another. At least one of the jaw members is pivotably coupled to the outer shaft and is movable between an open configuration and a clamping configuration for grasping tissue. The inner shaft contacts a proximal end of the moveable jaw member to maintain the movable jaw member in the open configuration and is slidable against the movable jaw member to move the moveable jaw member between the open configuration and clamping configuration. The inner shaft member includes at least one tine at a distal end thereof. The tine(s) are configured to selectively engage a corresponding longitudinal slot defined on an exterior top surface of the movable jaw member to move the moveable jaw member from the open configuration to the clamping configuration.

A pivot pin may be utilized to couple the pair of jaw members to one another. In this instance, an aperture may extend through the pivot pin and may be configured to receive a knife blade of the surgical apparatus therethrough to sever grasped tissue.

Both jaw members may be pivotably coupled to the outer shaft member and the inner shaft may contact a proximal end of both jaw members to maintain the jaw members in the open configuration. The moveable shaft member may be slidable against the jaw members to move the jaw members between the open and clamping configuration. The inner shaft member may include two tines at a distal end thereof configured to selectively engage corresponding longitudinal slots defined on an exterior top surface of jaw members to move jaw members from the open configuration to the clamping configuration. Moreover, a handle assembly may operably couple to the housing and have a movable handle that is operably coupled to the inner shaft member to effectuate movement thereof along the longitudinal axis defined through the shaft assembly.

An aspect of the present disclosure provides an electrosurgical forceps having a housing including a handle assembly having fixed and moveable handles. A shaft assembly is supported on the housing and defines a longitudinal axis therethrough. The shaft assembly includes coaxially aligned outer and inner shaft members. The inner shaft member is movable within the outer shaft member when the moveable handle is actuated to effectuate grasping tissue. The moveable shaft member has at least one cam member disposed at a distal end thereof. An end effector includes a pair of jaw members pivotably coupled to one another and disposed at a distal end of the outer shaft member. At least one of the jaw members is movable from an open configuration to a clamping configuration. The movable jaw member(s) includes an arcuate portion defined at the proximal end thereof. The cam member(s) resides in the arcuate portion of the moveable jaw member to maintain the movable jaw member in the open configuration and to move the moveable jaw member between the open configuration and clamping configuration when the movable handle is actuated. A pivot pin may be utilized to couple the pair of jaw members to one another.

The inner shaft member may include one or more cam members that extend transversely thereacross at a distal end thereof. The cam member(s) may be a cam pin. Alternatively, cam member(s) may be integrally formed with the inner shaft member. The cam member may reside in an arcuate portion defined at the proximal end of the moveable jaw member and may be moveable within the arcuate portion such that contact between the cam member and a proximal end of the arcuate portion moves the moveable jaw member from the open configuration to the clamping configuration.

The inner shaft member may include two cam members that extend transversely thereacross at a distal end thereof. The cam members may reside in arcuate portions defined at the proximal end of the jaw members and may be moveable within the arcuate portions such that contact between the cam members and a proximal end of the arcuate portions moves the jaw members from the open configuration to the clamping configuration.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
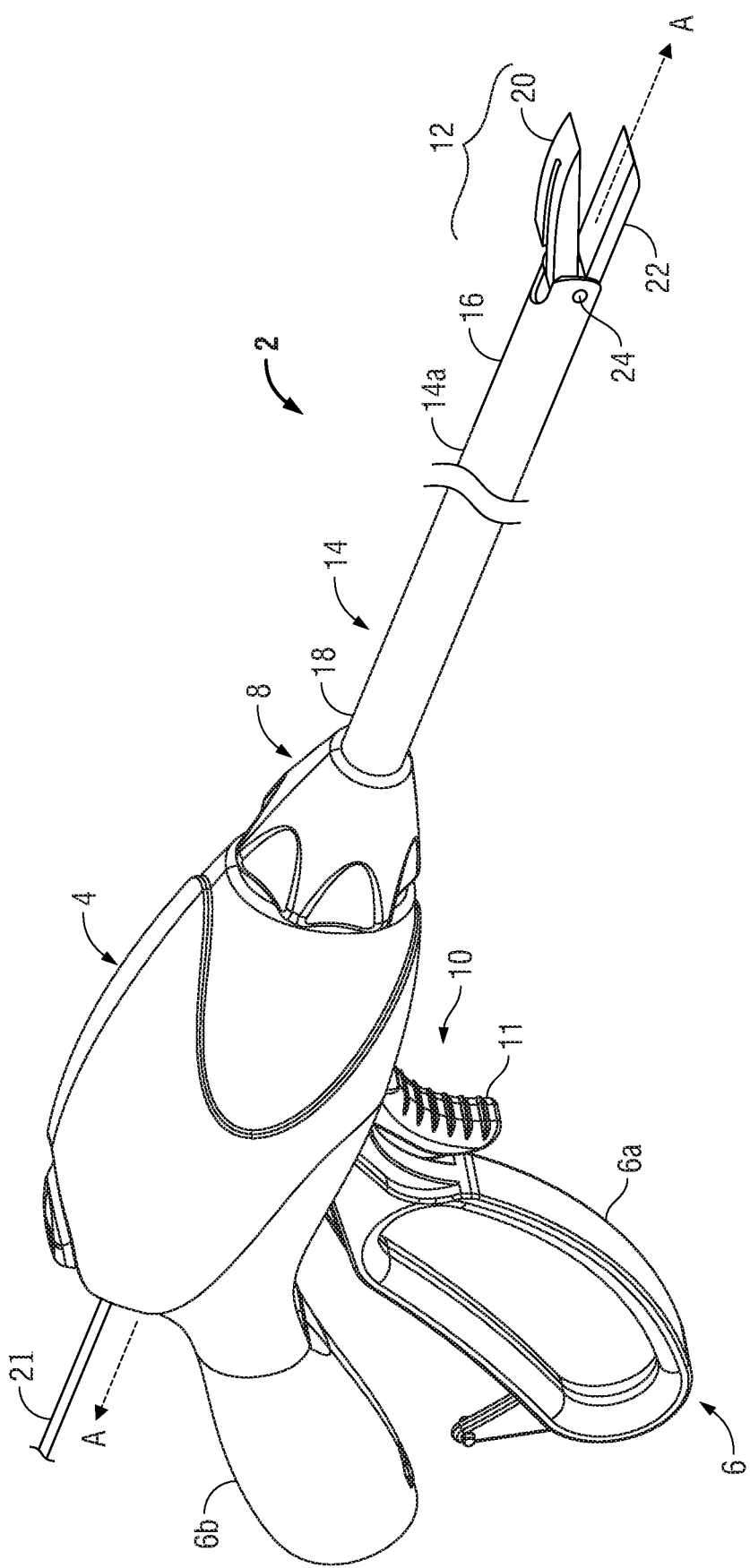
FIG. 1 is a right, perspective view of an endoscopic bipolar forceps according to an embodiment of the present disclosure.

Turning now to FIG. 1 a surgical apparatus, e.g., an endoscopic electrosurgical forceps 2 (forceps 2), according to an embodiment of the present disclosure is illustrated. Forceps 2 includes a housing 4, a handle assembly 6 including a movable handle 6a and fixed handle 6b, a rotating assembly 8, a trigger assembly 10 and an end effector assembly 12. In the illustrated embodiment, forceps 2 also includes electrosurgical cable 21 that connects forceps 2 to a generator (not explicitly shown) or other suitable power source. Electrosurgical cable 21 includes a wire (or wires) (not shown) extending therethrough that has sufficient length to extend through shaft 14 in order to provide electrical energy to one or both jaw members 20, 22 of end effector assembly 12. Alternatively, forceps 2 may be battery-powered. In this instance, a removable generator and battery assembly may be configured to power the forceps 2.

Figure 2:
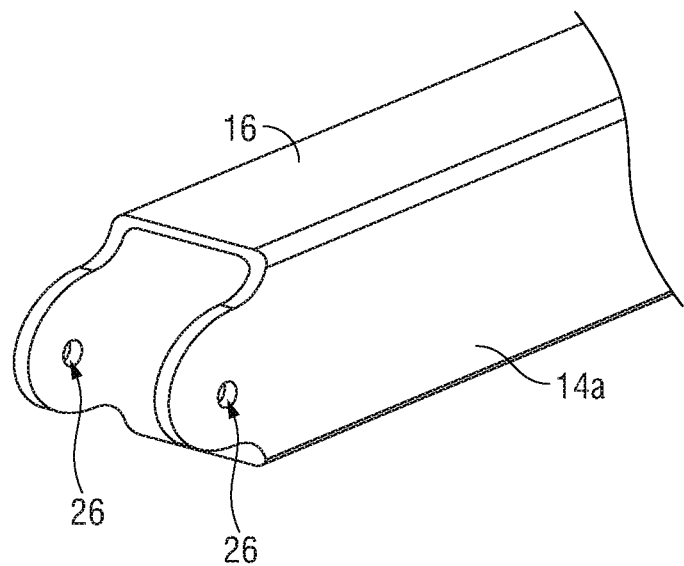
FIG. 2 is a side, perspective view of a distal end of an outer shaft depicted in FIG. 1 with jaw members removed.

With reference to FIGS. 1-2, a shaft assembly 14 including an outer shaft 14a (shaft 14a) is illustrated. Shaft 14a includes a distal end 16 that is configured to mechanically engage end effector assembly 12 and a proximal end 18 that mechanically engages housing 4 (FIGS. 1 and 2). Shaft 14a may be formed of any suitable material including, but not limited to metal, ceramic, plastic, etc. In the illustrated embodiment, shaft 14a is formed from metal, e.g., surgical steel.

One or both of jaw members 20, 22 are pivotably coupled to distal end 16 of shaft 14a. In the embodiment illustrated in FIGS. 1-8, shaft 14a pivotably couples to jaw member 20 via a pivot pin 24 (FIGS. 1 and 6-8) that extends through a pair of apertures 26 of suitable configuration defined through distal end 16 of shaft 14, as best seen in FIG. 2.

Pivot pin 24 may be made from any suitable material including the materials utilized to form shaft 14a, e.g., surgical steel. In some embodiments, such as embodiments where forceps 2 utilizes a knife blade 28 (FIG. 6) to sever treated tissue, pivot pin 24 may be formed with an aperture 30 of suitable configuration therethrough to receive knife blade 28 therein when trigger 11 (FIG. 1) of trigger assembly 10 is actuated. As a result of the unique configuration of pivot pin 24, knife blade 28 may be formed without "webbing," which, in turn, may provide knife blade 28 with increased structural integrity when compared to knife blades that are typically associated with conventional forceps. Additionally, the cost of manufacturing knife blade 28 (and/or forceps 2) in accordance with the instant disclosure may be less when compared to knife blades that are typically associated with conventional forceps. That is, the additional step of forming "webbing" through knife blade 28 is not required during manufacture of knife blade 28.

Figure 3:
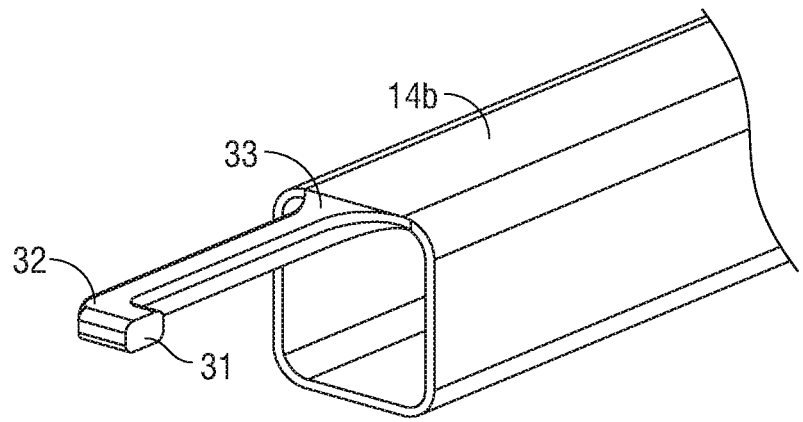
FIG. 3 is a side, perspective view of a distal end of an inner shaft of the endoscopic bipolar forceps depicted in FIG. 1.
Figure 7:
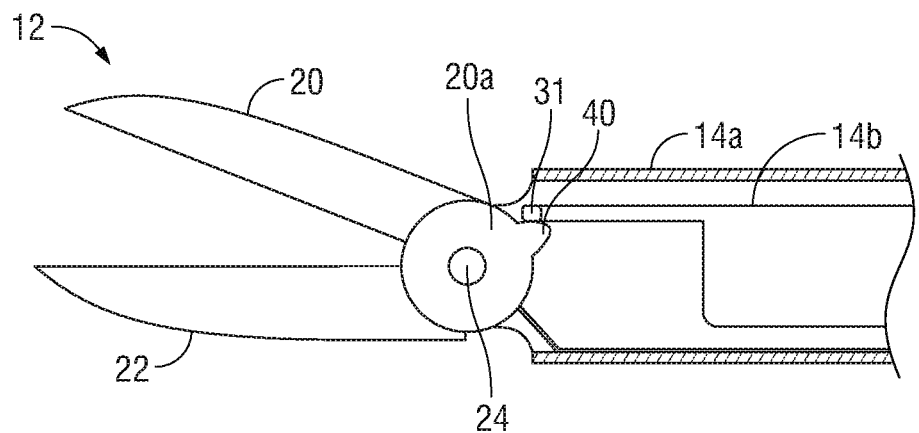
FIG. 7 is a side view of the jaw members depicted in FIG. 1 illustrated in an open configuration.
Figure 8:
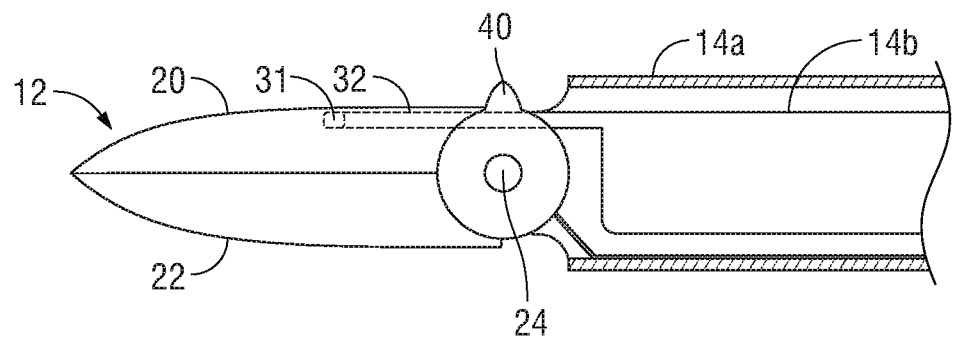
FIG. 8 is a side view of the jaw members depicted in FIG. 1 illustrated in a closed configuration.
Figure 9:
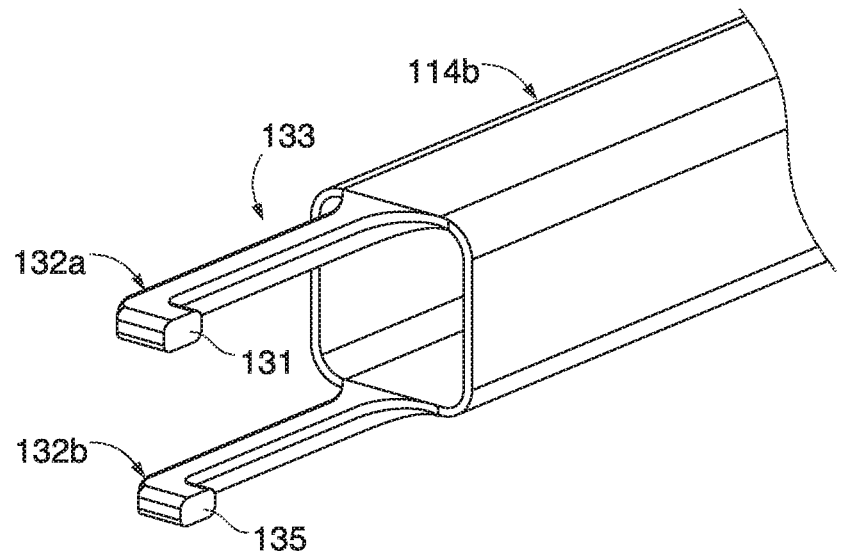
FIG. 9 is a side, perspective view of an inner shaft according to another embodiment of the present disclosure and configured for use with the endoscopic bipolar forceps depicted in FIG. 1.

With reference now to FIG. 3, shaft assembly 14 also includes an inner shaft 14*b* (shaft 14*b*). Shaft 14*b* may be formed of any suitable material, e.g., surgical steel, and is coaxially disposed within shaft 14*a* (see FIGS. 7 and 8 for example). Shaft 14*b* is movable with respect to shaft 14*a* when movable handle 6*a* is moved proximally to effectuate movement of one or both of jaw members 20, 22. Shaft 14*b* is configured to contact a proximal end 20*a* (FIGS. 4 and 7) of jaw member 20 to maintain jaw member 20 in an open configuration (FIGS. 1 and 7) and is slidable there against to move jaw member 20 between the open configuration and a clamping configuration (FIG. 8). In one embodiment, shaft 14*b* includes a generally tubular configuration having one or more tines 32 (FIG. 3) formed at a distal end 33 thereof. The tubular configuration of shaft 14*b* allows knife blade 28 to translate through shaft 14*b* when trigger 11 is actuated.

Figure 4:
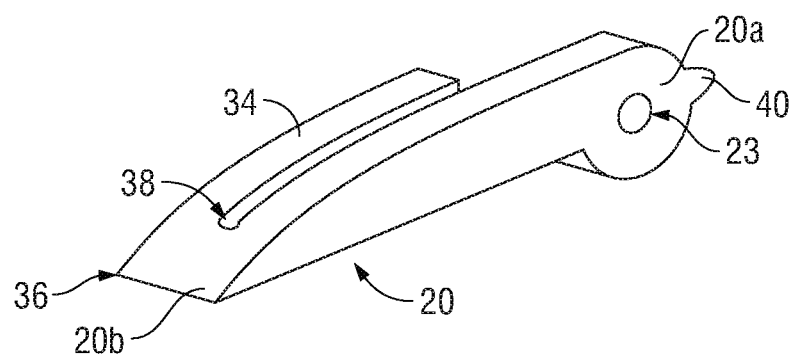
FIG. 4 is a side, perspective view of a movable jaw member depicted in FIG. 1.

Continuing with reference to FIG. 3, tine 32 includes a generally elongated configuration having a distal tip with an inwardly extending flange 31 that is slidable against an exterior surface 34 of a jaw housing 36 of jaw member 20 (FIGS. 3 and 4). In particular, when movable handle 6*a* is moved proximally, shaft 14*b* is configured to translate distally, which, in turn, moves flange 31 of tine 32 out of contact with proximal end 20*a* of jaw member 20 and into engagement with a corresponding longitudinal slot 38 defined on exterior surface 34 of jaw member 20 (FIG. 4). Movement of tine 32 within slot 38 moves jaw member 20 from the open configuration to the clamping configuration (and vice versa).

Tine 32 may be monolithically formed with shaft 14*b* or may be formed as a separate component from shaft 14*b* and, subsequently, coupled via one or more suitable coupling methods, e.g., ultrasonic welding, to distal end 33 of shaft 14*b*.

Figure 5:
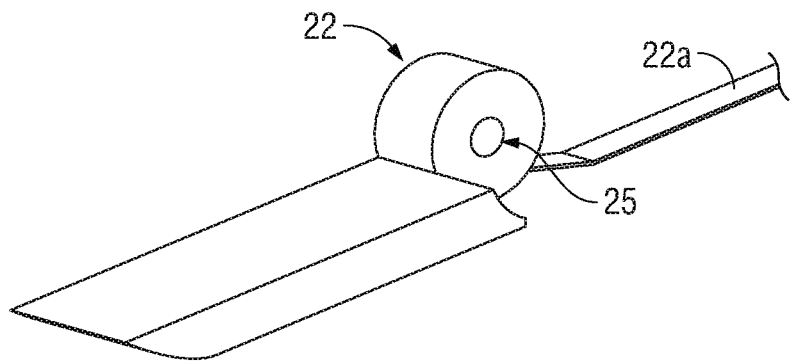
FIG. 5 is a side, perspective view of a stationary jaw member depicted in FIG. 1.
Figure 6:
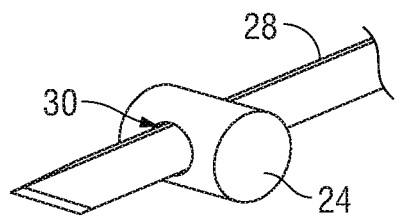
FIG. 6 is a side, perspective view of a pivot pin utilized to couple the jaw members depicted in FIG. 1.

Referring now to FIGS. 4 and 5, jaw members 20, 22 are illustrated respectively. End effector 12 is illustrated having jaw members 20, 22 that are operable in a bipolar mode configuration, e.g., both jaw members 20, 22 are configured to provide electrosurgical energy to tissue. In this instance, jaw members 20, 22 are operable as active and return electrodes. Alternatively, in a monopolar mode configuration, one of jaw members 20, 22 may be configured to function as the active electrode and a return pad (not explicitly shown) may be configured to function as the return electrode and utilized to provide a return path to the generator for electrosurgical energy.

In the embodiment illustrated in FIGS. 1-8, end effector 12 is shown including jaw members 20, 22 that are operable in a unilateral configuration. That is, jaw member 20 is movable with respect to jaw member 22 and shaft 14*a* from the open configuration to the clamping configuration when movable handle 6*a* is moved proximal. Alternatively, end effector 12 may be operable in a bilateral configuration where both jaw members 20, 22 may be movable with respect to each other from the open configuration to the clamping configuration when movable handle 6*a* is moved proximal, as described in more detail below.

Referring again to FIG. 4, slot 38 may be formed during an overmolding process of jaw housing 36 to jaw member 20. Alternatively, a machining process may be utilized to form slot 38 into exterior surface 34 of jaw housing 36 subsequent to overmolding jaw housing 36 to jaw member 20. Slot 38 extends substantially along a length of exterior surface 34 and is aligned with tine 32 such that as shaft 14*b* is moved distally, tine 32 moves distally and engages slot 38 to move jaw member 20 from the open configuration to the clamping configuration (see FIGS. 7 and 8).

Continuing with reference to FIG. 4, proximal end 20*a* is configured to selectively engage distal end 33 of shaft 14*b*. In particular, a protuberance 40 is provided at proximal end 20*a* of jaw member 20 and is configured to engage flange 31 of tine 32 when shaft 14*b* is in a retracted configuration. Engagement between protuberance 40 and flange 31 of tine 32 maintains jaw member 20 in the open configuration, as best seen in FIG. 7. Flange 31 is aligned with longitudinal slot 38 so as to laterally offset tine 32 from protuberance 40 which allows jaw member 20 including protuberance 40 to move from the open and clamping configurations without tine 32 and protuberance 40 interfering with one another.

In the illustrated embodiment, jaw member 22 is fixedly coupled to shaft 14*a* via one or more suitable coupling methods, e.g., ultrasonic welding. Jaw member 22 is coupled to shaft 14*a* such that shaft 14*b* is allowed to move from the retracted configuration disposed within shaft 14*a* (FIG. 7) to an extended configuration disposed outside of shaft 14*a* so that tine 32 may engage slot 38 (FIG. 8). In one particular embodiment, for example, a proximal end 22*a* of jaw member 22 may include a generally arcuate configuration that complements an interior surface of shaft 14*a* and may be ultrasonically welded to the interior surface of shaft 14*b*. This specific configuration allows shaft 14*b* to move over jaw member 22 from the retracted configuration to the extended configuration without interference from the jaw member 22. Those skilled in the art will appreciate alternative methods for coupling jaw member 22 to shaft 14*a*.

Apertures 23, 25 (FIGS. 4 and 5) extend through jaw members 20, 22, respectively, and are configured to receive pivot pin 24 therethrough such that jaw members 20, 22 are positioned in side-by-side fashion with respect to one another when in an assembled configuration (as best seen in FIG. 1). Alternatively, in some embodiments jaw member 22 may be provided without an aperture 25.

With reference again to FIG. 1, movable handle 6*a* is configured to effectuate movement of shaft 14*b* from the retracted configuration the extended configuration. One or more gears, links, servos, and the like may be utilized to couple movable handle 6*a* to shaft 14*b*. For example, and in one particular embodiment, a four-bar linkage system may be utilized to couple shaft 14*b* to movable handle 6*a*. In this particular embodiment, for example, proximal movement of movable handle 6*a* effectuates movement of a drive mechanism, e.g., a drive rod (not explicitly shown), which, in turn, moves shaft 14*b* distally.

In use, initially, flange 31 of tine 32 is engaged with protuberance 40 on jaw member 20 to maintain jaw member 20 in the open configuration (FIG. 7). Subsequently, tissue may be positioned between jaw members 20, 22 and movable handle 6*a* may be moved proximally. Proximal movement of movable handle 6*a* moves shaft 14*b* distally to the extended configuration. As shaft 14*b* moves distally, tine 32 including flange 31 moves out of engagement with protuberance 40 and into engagement with corresponding slot 38 on jaw member 20.

When tine 32 moves a predetermined distance, e.g., to distal end of slot 38, within slot 38, jaw member 20 moves to the clamping configuration to clamp the tissue positioned between jaw member 20 and jaw member 22 (FIG. 8). In the clamped configuration, tine 32 may be configured to provide a suitable closure force on the clamped tissue. For example, when tissue is to be sealed, tine 32 may be configured to provide a closure force on the clamped tissue that ranges from about 3 kg/cm$^2$ to about 16 kg/cm$^2$. In certain embodiments, however, such as, for example, in the instance where tissue is to coagulated, it may prove advantageous to provide a closure force on the clamped tissue that is less than 3 kg/cm$^2$ and/or greater than 16 kg/cm$^2$.

Electrosurgical energy from the generator may then be provided to jaw members 20, 22 to electrosurgically treat tissue. In some embodiments, knife blade 28 may be actuated to sever the treated tissue. In this particular embodiment, for example, trigger 11 of trigger assembly 10 may be actuated to translate knife blade 28 through aperture 30 of pivot pin 24 to sever the treated tissue.

The unique configuration of tine 32 and jaw member 20 allows a user to effectively clamp tissue between jaw members 20, 22 and, subsequently, treat the clamped tissue without the need of a camming member and cam pin that are typically associated with jaw members of conventional forceps.

From the foregoing and with reference to the various figure drawings, those skilled in the art will appreciate that certain modifications can also be made to the present disclosure without departing from the scope of the same. For example, and as noted above, in certain embodiments it may prove advantageous to utilize an end effector 12 that has two movable jaw members 20, 22.

With reference to FIGS. 9-13, an end effector 112 according to an alternate embodiment of the instant disclosure and configured for use with the forceps 2 is illustrated. Only the features unique to forceps 2 that utilize end effector 112 are described in further detail.

Figure 10A:
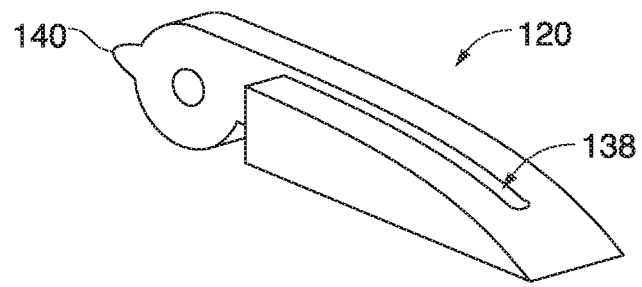
FIGS. 10A-10B are left and right side, perspective views of a movable jaw member configured for use with the moveable shaft depicted in FIG. 9.
Figure 10B:
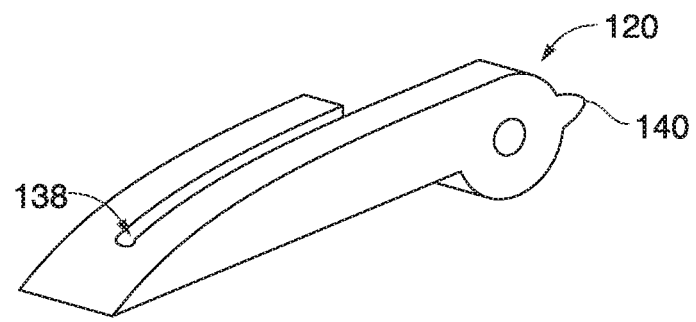
Figure 11A:
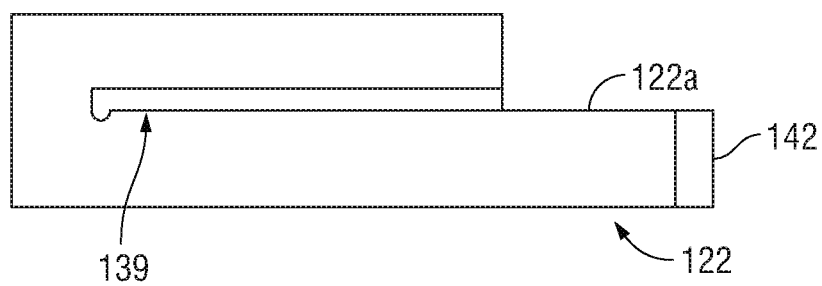
FIGS. 11A-11B are bottom and side plan views of a movable jaw member configured for use with the moveable shaft depicted in FIG. 9.
Figure 11B:
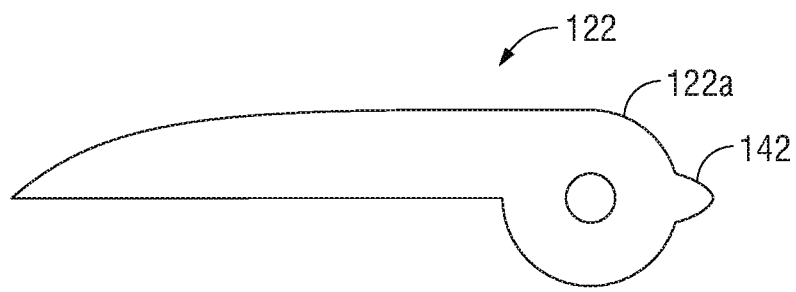
Figure 12:
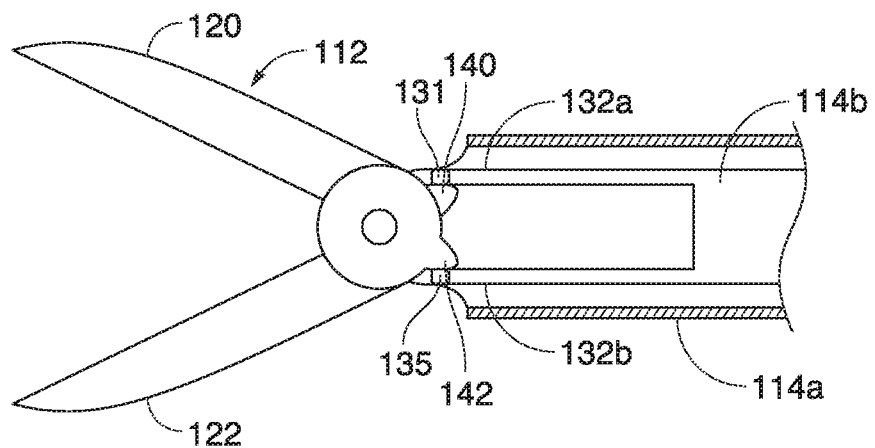
FIG. 12 is a side view of the jaw members depicted in FIGS. 10A-11B illustrated in an open configuration.
Figure 13:
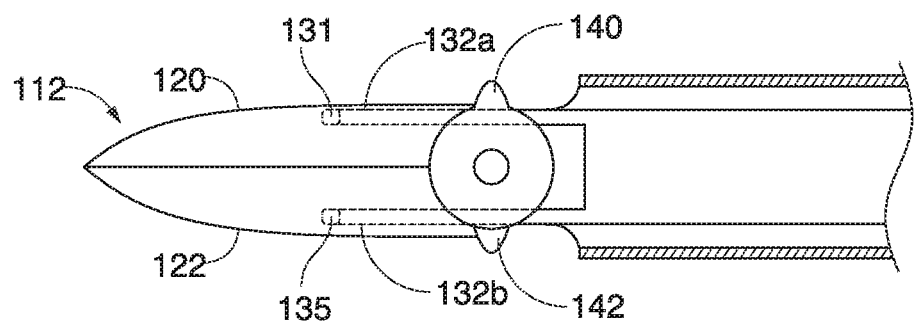
FIG. 13 is a side view of the jaw members depicted in FIGS. 10A-11B illustrated in a closed configuration.

In the embodiment illustrated in FIGS. 9-13, jaw member 122 (FIGS. 11A-11B) is configured to move from the open configuration (FIG. 12) to the clamping configuration (FIG. 13). Therefore, unlike shaft assembly 14, shaft assembly 114 includes shaft 114a that is configured to pivotably couple to both jaw members 120, 122 (FIG. 12).

Shaft 114b includes a bifurcated distal end 133 having a pair of tines 132a and 132b (FIG. 9) configured to engage corresponding slots 138 and 139 disposed on jaw members 120, 122 (FIGS. 10A-10B and 11A). Tines 132a and 132b including respective flanges 131, 135 are configured to function similar to that of tine 32. In view thereof, tines 132a and 132b are not described in further detail. Other than being disposed on jaw member 122 and configured to engage a tine 132b, slot 139 is identical to slot 138. In view thereof, slot 139 is not described in further detail.

Unlike jaw member 22, jaw member 122 includes a proximal end 122a having a protuberance 142 that is configured to engage tine 132b (FIGS. 11A-11B). Engagement of protuberance 142 with flange 135 of tine 132b maintains jaw member 122 in the open configuration, see FIG. 12 for example.

In use, initially, flanges 131, 135 of tines 132a, 132b, respectively, are engaged with protuberances 140, 142 on jaw members 120, 122 to maintain jaw members 120, 122 in the open configuration (FIG. 12). Subsequently, tissue may be positioned between jaw members 120, 122 and movable handle 6a may be moved proximally. Proximal movement of movable handle 6a moves shaft 114b distally to the retracted configuration. As shaft 114b moves distally, tines 132a, 132b move out of engagement with protuberances 140, 142 and into engagement with corresponding slots 138, 139 on jaw members 120, 122.

When tines 132a, 132b move a predetermined distance within slots 138, 139, jaw members 120, 122 move to the clamping configuration to clamp the tissue positioned between jaw member 120 and jaw member 122 (FIG. 13). In the clamped configuration, tines 132a, 132b may be configured to provide one or more of the aforementioned suitable closure forces on the clamped tissue.

Electrosurgical energy from the generator may then be provided to jaw members 120, 122 to electrosurgically treat tissue. In some embodiments, knife blade 28 may be actuated to sever the treated tissue. In this particular embodiment, for example, trigger 11 of trigger assembly 10 may be actuated to translate knife blade 28 through aperture 30 of pivot pin 24 to sever the treated tissue.

As can be appreciated, the same aforementioned advantages described above with respect to forceps 2 that utilizes one movable jaw member 20, may be obtained with forceps 2 that utilizes two movable jaw members 120, 122.

While the aforementioned forceps 2 have been described herein as including end effectors 12, 112 that cooperate with respective shaft assemblies 14, 114, other end effector and shaft assembly configurations may be utilized with forceps 2.

Figure 14:
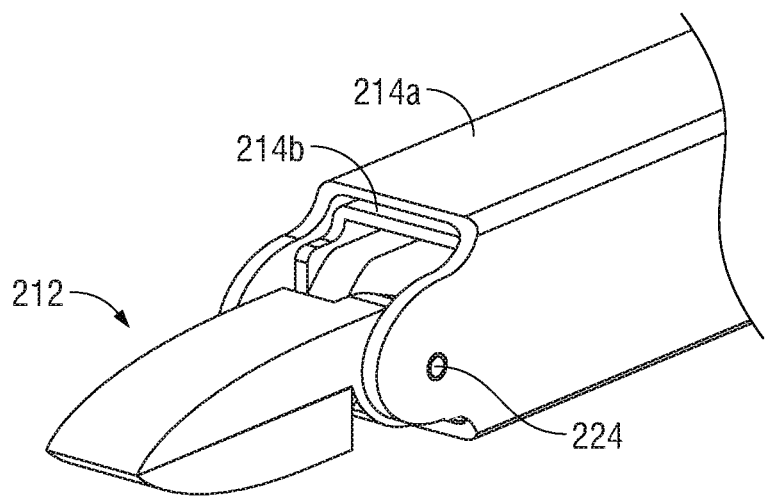
FIG. 14 is a side, perspective view of a distal end of an outer shaft according to another embodiment of the present disclosure and configured for use with the endoscopic bipolar forceps depicted in FIG. 1.
Figure 16:
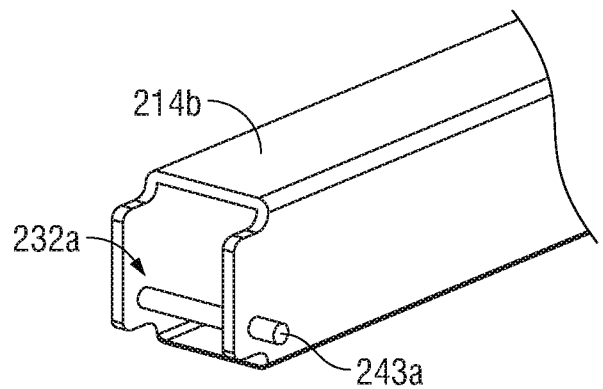
FIG. 16 is a side, perspective view of a distal end of an inner shaft associated with the distal end of the outer shaft depicted in FIG. 14.
Figure 17:
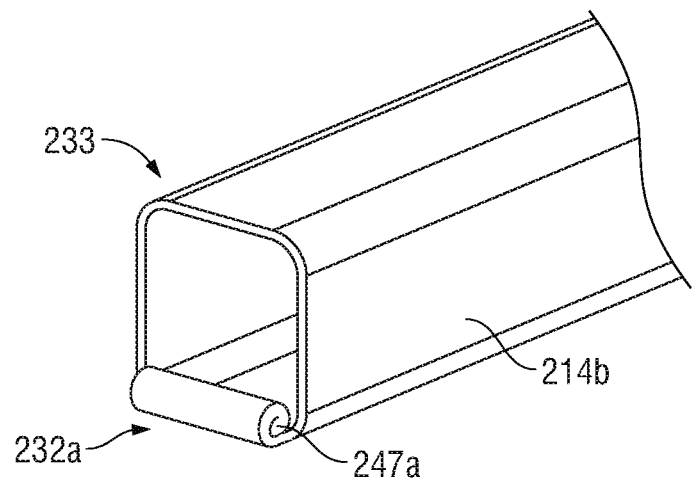
FIG. 17 is a side, perspective view of an inner shaft associated with of the distal end of the outer shaft depicted in FIG. 14 according to another embodiment.
Figure 18:
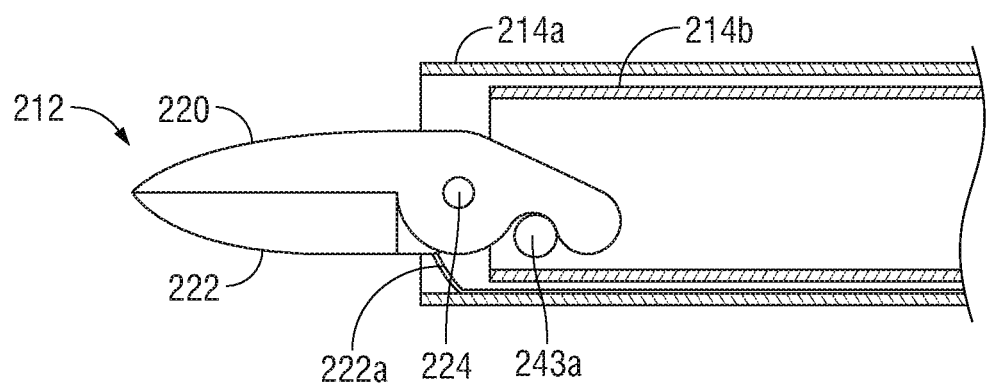
FIG. 18 is a side view of the jaw members depicted in FIGS. 15A and 15B illustrated in a closed configuration.
Figure 19:
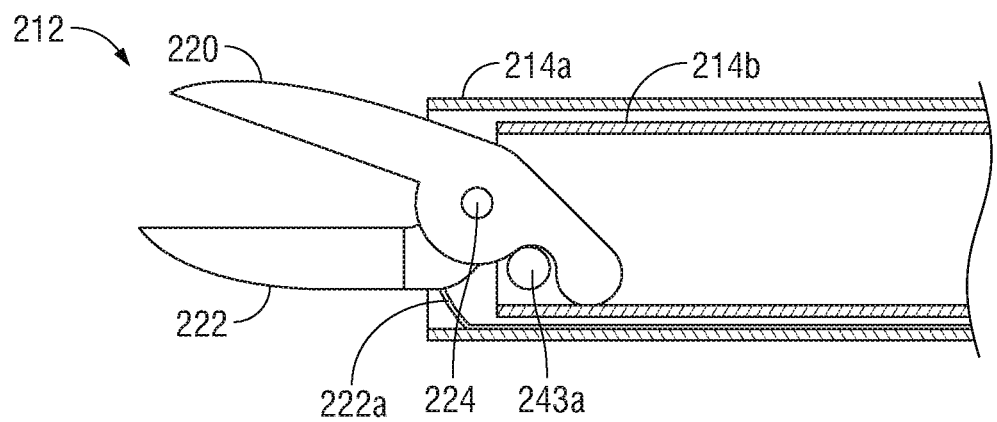
FIG. 19 is a side view of the jaw members depicted in FIGS. 15A and 15B illustrated in an open configuration.

With reference to FIGS. 14-17, end effector 212 is illustrated including two jaw members 220, 222. In the embodiment illustrated in FIGS. 14-17, end effector 212 utilizes a unilateral jaw configuration. In particular, jaw member 220 is movable with respect to shaft 214a about pivot pin 224 (FIGS. 14 and 18-19). Alternatively, a bilateral jaw configuration may be utilized, described in detail below.

Figure 15A:
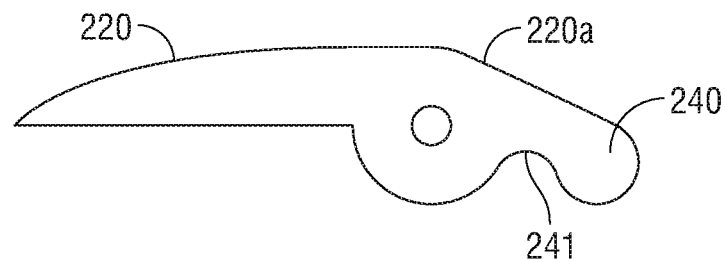
FIG. 15A is a side, perspective view of a movable jaw member depicted in FIG. 14.

Continuing with reference to FIG. 15A, jaw member 220 is illustrated including proximal end 220a having a generally arcuate notch 241 disposed adjacent protuberance 240. Notch 241 is configured to receive one or more camming structures 232a (FIGS. 16-17) therein.

Figure 20:
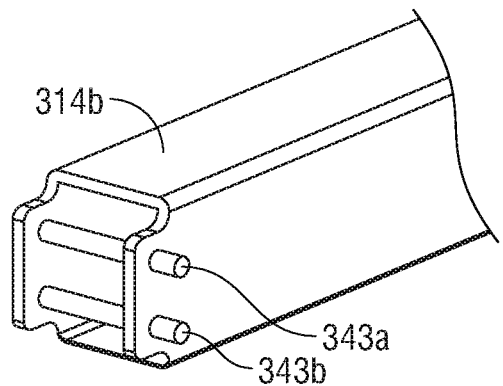
FIG. 20 is a side, perspective view of an inner shaft according to another embodiment of the present disclosure and configured for use with the outer shaft depicted in FIG. 14.

Camming structure 232a may be any suitable camming structure. For example, in the embodiment illustrated in FIG. 16, camming structure 232a is in the form of a cam pin 243a. Alternatively, distal end 233 of shaft 214b may have top and/or bottom rolled portions 247a as shown in FIG. 17. In the embodiments illustrated in FIGS. 16-17, cam pin 243a and rolled bottom portion 247a extend laterally across shaft 214b and seat within the notch 241. The cam pin 243a or rolled bottom portion 247a are configured to move within the confines of the notch 241 to move jaw member 220 between the open configuration and clamping configuration. In particular, when cam pin 243a (or rolled bottom portion 247a) is in a relatively distal position within notch 241, which corresponds to shaft 214b being in an extended configuration, jaw member 220 is maintained in the open configuration (FIG. 19). Likewise, when cam pin 243a (or rolled bottom portion 247a) is disposed in a relatively proximal position and adjacent (or in contact with) protuberance 240, which corresponds to shaft 214b being in a retracted configuration, jaw member 220 is maintained in the clamping configuration (FIG. 20).

Figure 15B:
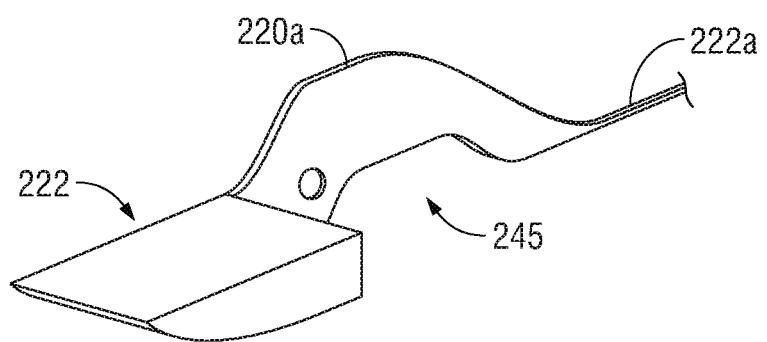
FIG. 15B is a side, perspective view of a stationary jaw member depicted in FIG. 14.

With reference to FIG. 15B, jaw member 222 is illustrated. Jaw member 222 includes a generally arcuate bottom portion 245 that is configured to facilitate movement of camming structure 232a within notch 241. In particular, in an assembled configuration proximal end 222a couples to the shaft 214a via one or more of the aforementioned coupling methods, e.g., ultrasonic welding, and one of the aforementioned camming structures 232a is positioned within an area defined by arcuate bottom portion 245. The arcuate bottom portion 245 allows shaft 214b to move from the extended configuration to the retracted configuration without interference from jaw member 222, see FIGS. 18 and 19 for example.

Operation of forceps 2 that includes end effector 212 is described herein with respect to camming structure 232a including cam pin 243a (FIG. 16).

In use, initially, shaft 214b is in the extended configuration and cam pin 243a is in a relatively distal position within notch 241 to maintain jaw member 220 in the open configuration (FIG. 19). Subsequently, tissue may be positioned between jaw members 220, 222 and movable handle 6a may be moved proximally. Proximal movement of movable handle 6a moves shaft 214b proximally to the retracted configuration. As shaft 214b moves a predetermined distance proximally, cam pin 243a moves into engagement with protuberance 240, which, in turn, moves jaw member 220 to the clamping configuration to clamp the tissue positioned between jaw member 220 and jaw member 222 (FIG. 18). In the clamped configuration, cam pin 243a may be configured to provide one or more of the aforementioned suitable closure forces on the clamped tissue.

Electrosurgical energy from the generator may then be provided to jaw members 220, 222 to electrosurgically treat tissue. In some embodiments, knife blade 28 may be actuated to move through aperture 30 of pivot pin 224 to sever the treated tissue.

As can be appreciated, the same aforementioned advantages described above with respect to forceps 2 that utilizes end effectors 12, 112, may be obtained with forceps 2 that utilizes end effector 212.

With reference to FIGS. 20-23, end effector 312 that utilizes a bilateral jaw configuration is illustrated. Only those features unique to end effector 312 and shaft assembly 314 are described in detail.

Figure 21:
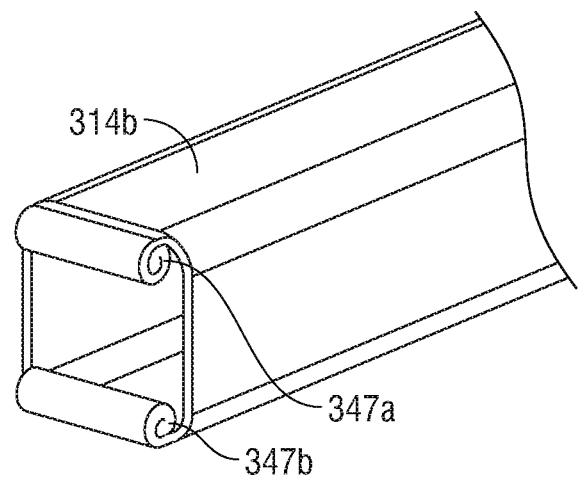
FIG. 21 is a side, perspective view of an inner shaft according to another embodiment of the present disclosure and configured for use with the outer shaft depicted in FIG. 14.
Figure 22:
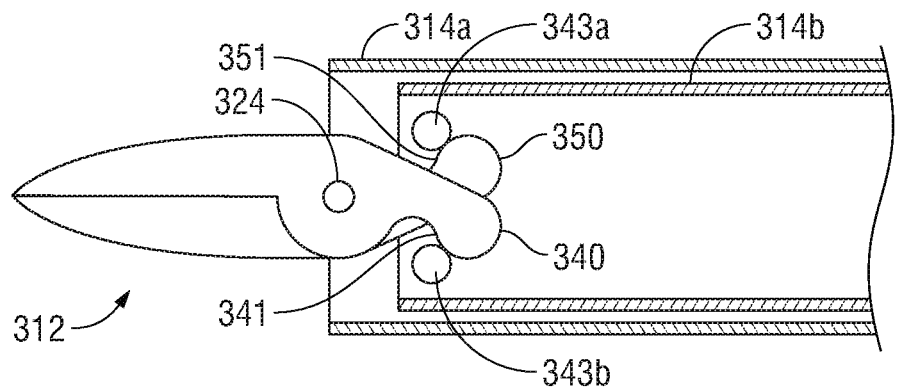
FIG. 22 is a side view of jaw members configured for use with the inner shaft assemblies depicted in FIGS. 20 and 21 and the illustrated in a closed configuration.

With reference to FIGS. 20 and 21, shaft 314b may include a pair of top and bottom cam pins 343a, 343b or a pair of top and bottom rolled portions 347a, 347b configured to seat within respective notches 341, 351 (FIGS. 22-23) on jaw members 320, 322.

Jaw member 322 couples to shaft 314a via pivot pin 324 (FIGS. 22-23) and includes protuberance 350 at a proximal end thereof.

Figure 23:
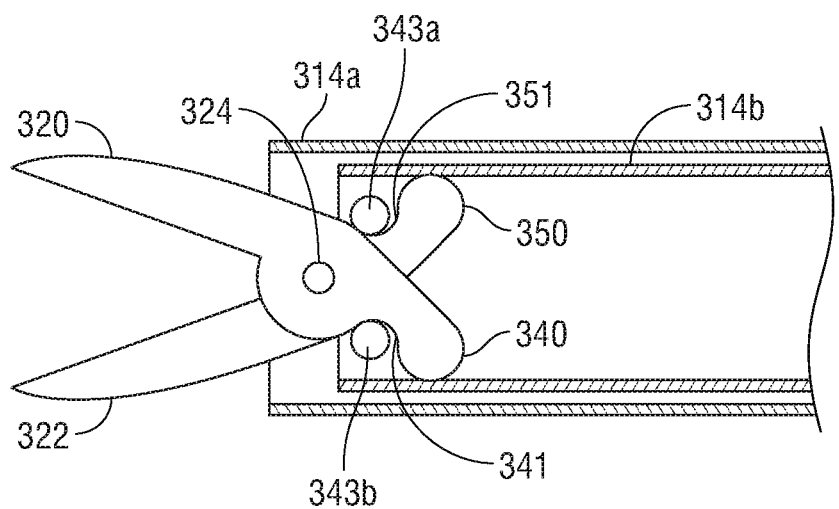
FIG. 23 is a side view of jaw members configured for use with the inner shaft assemblies depicted in FIGS. 20 and 21 and the illustrated in an open configuration.

In use, initially, shaft 314b is in the extended configuration and cam pins 343a, 343b are in a relatively distal position within notches 341, 351 to maintain jaw members 322, 320 in the open configuration (FIG. 23). Subsequently, tissue may be positioned between jaw members 320, 322 and movable handle 6a may be moved proximally. Proximal movement of movable handle 6a moves shaft 314b proximally to the retracted configuration. As shaft 314b moves a predetermined distance proximally, cam pins 343a, 343b move into engagement with protuberances 350, 340 which, in turn, moves jaw members 322, 320 to the clamping configuration to clamp the tissue positioned between jaw member 320 and jaw member 322 (FIG. 23). In the clamped configuration, cam pins 343a, 343b may be configured to provide one or more of the aforementioned suitable closure forces on the clamped tissue.

Electrosurgical energy from the generator may then be provided to jaw members 320, 322 to electrosurgically treat tissue. In some embodiments, knife blade 28 may be actuated to move through aperture 30 of pivot pin 324 to sever the treated tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic electrosurgical forceps, comprising:
   a housing including a handle assembly having fixed and movable handles;
   a shaft assembly supported on the housing and defining a longitudinal axis therethrough and including coaxially aligned outer and inner shaft members, the inner shaft member movable within the outer shaft member when the movable handle is actuated to effectuate grasping tissue, the inner shaft member having at least one cam member disposed at a distal end thereof, the inner shaft member having a tubular configuration defining a lumen therein;
   an end effector including a pair of jaw members pivotably coupled to one another and disposed at a distal end of the outer shaft member, at least one of the jaw members movable from an open configuration to a clamping configuration, the at least one jaw member including an arcuate notch defined at a proximal end thereof, the arcuate notch of the at least one jaw member positioned in the lumen of the inner shaft member; and
   a knife blade independently movable relative to the inner shaft member,
   wherein the at least one cam member resides in the arcuate notch of the at least one jaw member to maintain the at least one jaw member in the open configuration and to move the at least one jaw member between the open configuration to the clamping configuration when the movable handle is actuated.

2. The endoscopic electrical forceps according to claim 1, wherein the at least one cam member extends transversely across inner sidewalls of the inner shaft member.

3. The endoscopic electrical forceps according to claim 2, wherein the at least one cam member is a cam pin.

4. The endoscopic electrical forceps according to claim 2, wherein the at least one cam member is integrally formed with the inner shaft member.

5. The endoscopic electrical forceps according to claim 2, wherein the at least one cam member is movable within the arcuate notch such that contact between the at least one cam member and a proximal end of the arcuate notch moves the at least one jaw member from the open configuration to the clamping configuration.

6. The endoscopic electrical forceps according to claim 1, wherein the inner shaft member includes a second cam member, the first and second cam members extending transversely across the inner shaft member, the first and second cam members residing in arcuate notches defined at the proximal ends of each of the jaw members and movable within the arcuate notches such that contact between the first and second cam members and respective proximal ends moves the jaw members from the open configuration to the clamping configuration.

7. The endoscopic electrosurgical forceps according to claim 1, wherein a pivot pin couples the pair of jaw members to one another.

8. A forceps, comprising:
   a housing including a fixed handle and a movable handle;
   an outer shaft member extending from the housing and defining a longitudinal axis;

an end effector including a first jaw member and a second jaw member supported by the outer shaft member adjacent a distal portion thereof, the first jaw member movable relative to the second jaw member to transition the end effector between an open configuration and a clamping configuration, the first jaw member having a first arcuate notch defined adjacent a proximal portion thereof;

an inner shaft member having a tubular configuration defining a lumen therein, the inner shaft member coaxially aligned with the outer shaft member and translatable along the longitudinal axis relative to the outer shaft member, the inner shaft member translating in response to actuation of the movable handle relative to the fixed handle, the inner shaft member including a first cam member disposed adjacent a distal portion of the inner shaft member, the first cam member residing in the first arcuate notch to maintain the end effector in the open configuration and to move the first jaw member in response to actuation of the movable handle to transition the end effector to the clamping configuration, the first arcuate notch positioned in the lumen of the inner shaft member; and a knife blade independently movable relative to the inner shaft member.

9. The forceps according to claim 8, wherein the first cam member extends transversely across inner sidewalls of the inner shaft member.

10. The forceps according to claim 9, wherein the first cam member is a cam pin.

11. The forceps according to claim 9, wherein the first cam member is integrally formed with the inner shaft member.

12. The forceps according to claim 9, wherein the first cam member is movable within the first arcuate notch such that contact between the first cam member and the first arcuate notch moves the end effector from the open configuration to the clamping configuration.

13. The forceps according to claim 12, wherein the first arcuate notch includes a first protuberance positioned at a proximal end thereof, the first cam member engaging the first protuberance to move the end effector from the open configuration to the clamping configuration.

14. The forceps according to claim 8, wherein the inner shaft member includes a second cam member extending transversely thereacross, the second cam member residing in a second arcuate notch defined adjacent a proximal portion of the second jaw member, the second cam member movable within the second arcuate notch such that contact between the second cam member and the second arcuate notch transitions the end effector from the open configuration to the clamping configuration.

15. The forceps according to claim 14, wherein the second arcuate notch includes a second protuberance positioned at a proximal end thereof, the second cam member engaging the second protuberance to move the end effector from the open configuration to the clamping configuration.

16. The forceps according to claim 8, wherein a pivot pit couples the first and second jaw members to one another.

17. The forceps according to claim 8, wherein the second jaw member is fixed relative to the outer shaft member.

* * * * *